United States Patent [19]

Paget, Jr.

[11] 4,088,770

[45] May 9, 1978

[54] SUBSTITUTED 2-ANILINOBENZOXAZOLES USED AS IMMUNOSUPPRESSIVE AGENTS

[75] Inventor: Charles J. Paget, Jr., Indianapolis, Ind.

[73] Assignee: Eli Lilly and Company, Indianapolis, Ind.

[21] Appl. No.: 419,733

[22] Filed: Nov. 28, 1973

Related U.S. Application Data

[63] Continuation-in-part of Ser. No. 255,702, May 22, 1972, abandoned, which is a continuation-in-part of Ser. No. 188,544, Oct. 12, 1971, abandoned, which is a continuation-in-part of Ser. No. 140,289, May 4, 1971, abandoned.

[51] Int. Cl.² ............................................. A61K 31/42
[52] U.S. Cl. ...................................... 424/272; 71/88
[58] Field of Search ......................................... 424/272

[56] References Cited

U.S. PATENT DOCUMENTS 2,886,572  5/1959  Engelhardt ........................... 260/307

3,822,356  7/1974  Brenneisen et al. ................. 424/272

OTHER PUBLICATIONS

Physician's Desk Reference (PDR), 1974, pp. 651–652.
Deck et al., J. Amer. Chem. Soc., 55, 4986–4987, 4991 (1933).
Cerniani et al., Chemical Abstracts, 49:4626f (1955).
Passerini Chemical Abstracts, 49:10266h,i, –10267a (1955).
Kurzer et al., J. Chem. Soc. (1963), pp. 240–241, 245.
Sam et al., Chemical Abstracts, 69:96536e (1968).

Primary Examiner—Leonard Schenkman
Attorney, Agent, or Firm—Ralph W. Ernsberger; Everet F. Smith

[57] ABSTRACT

Compositions comprising certain 2-(substituted anilino)benzoxazoles, such as 2-[4-bromo-3-(trifluoromethyl)anilino]benzoxazole, and methods for using same as immunosuppressive agents, antifertility agents, for the prophylaxis of Marek's disease in chickens and as herbicides.

6 Claims, No Drawings

SUBSTITUTED 2-ANILINOBENZOXAZOLES USED AS IMMUNOSUPPRESSIVE AGENTS

CROSS-REFERENCE

This application is a continuation-in-part of copending application Ser. No. 255,702, filed May 22, 1972, which was a continuation-in-part of copending application Ser. No. 188544, filed Oct. 12, 1971, which was a continuation-in-part of copending application Ser. No. 140,289, filed May 4, 1971, all of which are now abandoned.

BACKGROUND OF THE INVENTION

1. Field of the Invention

This invention relates to novel organic compounds. More particularly, this invention relates to certain 2-(substituted anilino)benzoxazoles, compositions thereof, and methods for using same in suppressing the immune response mechanism, controlling fertility, improving weight gains and reducing gross lesions in chickens exposed to Marek's disease, and as herbicides.

2. Description of the Prior Art

Considerable interest has developed in recent years in the physiological activity of 2-substitutedbenzoxazoles. Some urea derivatives of this class of compounds are described in the art. For example, N-(benzoxazoyl)-N'-$C_1$-$C_5$ aliphatic ureas are disclosed in U.S. Pat. No. 3,299,085 as intermediates in the preparation of certain herbicides. U.S. Pat. No. 3,162,644 describes 2-benzoxazoylureas useful as plant growth regulators and muscle relaxants. Paget, et al., have described the immunosuppressive activity of a number of benzoxazoleureas. [Paget, C. J.; Kisner, K.; Stone, R. L.; and DeLong, D. C.; J. Med. Chem., 12 1016 et seq. (1969)].

Deck, et al., reported the synthesis of 2-anilinobenzaxole [Deck and Dains, J. Amer. Chem. Soc., 55, 4986 (1933)].

Recently, immunosuppressive agents have come into prominence because of their use during organ transplants from one human to another, particularly in connection with heart and kidney transplants. It is part of the defense mechanism of humans to reject foreign antigens (in this case, the transplanted organ) by the immune reaction. Thus, in all of the organ transplant operations it has been necessary to give large doses of an immunosuppressive agent prior to the surgery and continuing thereafter in order to prevent the host from rejecting the donor organ. The present immunosuppressive agent of choice is azathioprine (U.S. Pat. No. 3,056,785).

In addition, a significant emphasis is developing on the population explosion. More reliable fertility control agents are needed to be used in overcoming the sky-rocketing birth rate in many underdeveloped countries of the world. More to the point is the desire to perfect a method for preventing the development of the fertilized ova, a "morning after" contraceptive as it were.

Moreover, Marek's disease is a debilitating disease which attacks avian species and is found throughout the world wherever chickens are present. The causative agent is thought to be a virus or viruses of the herpes type. The mode of infection is believed to be through the breathing or ingestion of the virus or by transmission from the hen via the fertile egg to the embryo. The incubation period for the disease is from four to six weeks. The disease includes all acute forms of avian leukosis that are characterized by a proliferation of pleomorphic lymphocytes and plasma cells. The lesions can be found in the nervous system, the eyes, the viscera, the skeletal muscle, and the skin. Marek's disease syndrome is said by Burmester and Witter, *An Outline of the Diseases of the Avain Leukosis Complex,* Production Research Report No. 94, United States Department of Agriculture (USDA) (1966), to encompass such clinical conditions as fowl paralysis, range paralysis, polyneuritis, neurolymphomatosis gallinarum, visceral lymphomatosis, acute leukosis, ocular lymphomatosis and iritis. The early manifestations of the disease are apparent in such conditions as failure to gain weight, dehydration, and paralysis. The disease may result in an early or lingering death or, if the bird survives the acute phase of the disease, a regression of the symptoms may take place, and the bird may recover. However, even recovered birds can contribute to substantial economic losses to the grower because they fall behind in the growth schedule. The economic loss to the poultry industry from Marek's disease is high. For example, it has been estimated that the incidence of Marek's disease in broiler flocks ranges up to 8 percent. In 1968, about 36 million broiler chickens damaged by Marek's disease were condemned in USDA-inspected processing plants. This figure represented about 48 percent of all condemnations reported in 1968 (USDA Statistical Reporting Service POW 2-1, Crop Reporting Board, Washington, D.C. 20250).

Until a short time ago, control procedures for Marek's disease were limited to maintenance of good hygiene and sanitation and to the development of strains of disease-resistant birds. More recently a prophylactic vaccine has been announced which comprises the parenteral administration of a turkey virus found to be nonpathogenic to chickens. U.S. Pat. No. 3,548,054 claims the use of parenterally administered live attenuated Newcastle disease virus vaccine to young chicks up to the seventh day after hatching for improving weight gains and reducing gross lesions in chickens exposed to Marek's disease. U.S. patent application Ser. No. 831,229 discloses the use of Statolon as a parenterally administered substance for the improvement of weight gains and the reduction of gross lesions in chickens exposed to Marek's disease. There are no disclosed methods for altering the pathogenesis of Marek's disease by orally administering an agent for the prophylaxis or treatment of Marek's disease.

It is an object of this invention to provide compositions and methods for suppressing the immune reaction in warm-blooded mammals employing 2-(substituted anilino)benzoxazoles as active agents. It is another object of this invention to provide methods for controlling fertility by administering certain 2-(substituted anilino)-benzoxazoles as active materials. It is a further object of this invention to provide compositions and methods for increasing weight gains and reducing gross lesions in chickens exposed to Marek's disease by employing certain 2-(substitutedanilino)benzoxazoles as active compounds.

SUMMARY OF THE INVENTION

It has now been discovered that certain 2-(substituted anilino)benzoxazoles are useful immunosuppressive agents when administered to warm-blooded mammals, and demonstrate an antifertility effect when injected into adult female rats. Some of the 2-(substituted anilino)benzoxazoles when administered orally to chickens daily from the time of hatching until the chickens are, in the case of broilers, five to six weeks old, and, in the case of layer chickens, 12 to 14 weeks old, have a prophylactic effect and are effective in improving weight gains and reducing gross lesions in chickens exposed to Marek's disease. Still others among these useful compounds are effective herbicides.

DESCRIPTION OF THE PREFERRED EMBODIMENTS

The novel compounds of this invention are those of the formula

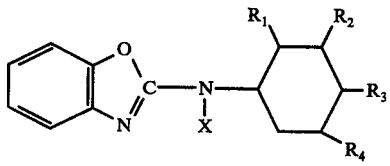

wherein,

X is hydrogen, $C_1$-$C_4$ alkyl, $C_1$-$C_3$ alkoxy, $C_1$-$C_3$ alkoxy $C_1$-$C_3$ alkyl, carboxy, carboxy $C_1$-$C_3$ alkyl, amino $C_1$-$C_3$ alkyl, mono-$C_1$-$C_3$ alkylamino $C_1$-$C_3$ alkyl, di-$C_1$-$C_3$ alkylamino $C_1$-$C_3$ alkyl, anilino $C_1$-$C_3$ alkyl, $C_1$-$C_3$ alkylthio, $C_1$-$C_3$ alkylsulfonyl, phenyl, phenyl $C_1$-$C_3$ alkyl, or carbanilino;

$R_1$, $R_2$, $R_3$, and $R_4$, when only one is a substituent other than hydrogen, are trifluoromethyl, carboxy, carboxy $C_1$-$C_3$ alkyl, $C_1$-$C_3$ alkoxy $C_1$-$C_3$ alkyl, carb $C_1$-$C_3$ alkoxy, $C_1$-$C_3$ alkylthio, $C_1$-$C_3$ alkylsulfonyl, or phenyl;

$R_1$, $R_2$, $R_3$, and $R_4$, when any two are substituents other than hydrogen are bromine, chlorine, fluorine, trifluoromethyl, carboxy, $C_1$-$C_3$ alkyl, $C_1$-$C_3$ alkoxy, carboxy $C_1$-$C_3$ alkyl, $C_1$-$C_3$ alkoxy $C_1$-$C_3$ alkyl, carb $C_1$-$C_3$ alkoxy, $C_1$-$C_3$ alkylthio, $C_1$-$C_3$ alkylsulfonyl, phenyl, or nitro, with the proviso that only one of the two substituents other than hydrogen is either nitro or phenyl; and with the further proviso that when X is other than hydrogen, all of $R_1$, $R_2$, $R_3$, and $R_4$ can be hydrogen.

The novel compounds of this invention are distinguished in all cases by either a single or double substitution in the phenyl ring of the anilino moiety such that the substitutedanilino moiety can be described by the structural designation: 2-(2-, or 3-, or 4-, or 2,3-, or 2,4-, or 3,4-, or 2,5-, or 3,5- substitutedanilino)benzoxazole. Preferred compounds are those named as follows:

2-(3-fluoro-4-nitroanilino)benzoxazole
2-(4-bromo-3-methylanilino)benzoxazole
2-(2-bromo-4-methylanilino)benzoxazole
2-(3-carboxyanilino)benzoxazole
2-(3-bromo-5-methylanilino)benzoxazole
2-(4-carboxyanilino)benaoxazole
2-[3-(methylthio)anilino]benzoxazole
2-[3-(methylsulfonyl)anilino]benzoxazole
2-[2-trifluoromethyl)anilino]benzoxazole
2-[3-trifluoromethyl)anilino]benzoxazole
2-(2-methyl-5-nitroanilino)benzoxazole
2-(3,4-dichloroanilino)benzoxazole
2-(2,5-dichloroanilino)benzoxazole
2-(2,3-dichloroanilino)benzoxazole
2-(2,5-difluoroanilino)benzoxazole
2-[2-bromo-5-(trifluoromethyl)anilino]benzoxazole
2-[4-bromo-2-(trifluoromethyl)anilino]benzoxazole
2-[4-chloro-2-(trifluoromethyl)anilino]benzoxazole
2-[4-fluoro-2-(trifluoromethyl)anilino]benzoxazole
2-[N-benzyl-3-(trifluoromethyl)anilino]benzoxazole
2-[3-(trifluoromethyl)-N-methylanilino]benzoxazole
2-[N-(n-butyl)-3-(trifluoromethyl)anilino]benzoxazole
2-[4-chloro-3-(trifluoromethyl)-N-methylanilino]benzoxazole
2-[N-benzyl-4-chloro-3-(trifluoromethyl)anilino]benzoxazole
2-[4-(trifluoromethyl)-2-nitroanilino]benzoxazole
2-[4-bromo-3-(trifluoromethyl)anilino]benzoxazole
2-[5-(trifluoromethyl)-2-methylanilino]benzoxazole Especially preferred are the compounds:
2-(2,4-dichloroanilino)benzoxazole
2-[4-bromo-3-(trifluoromethyl)anilino]benzoxazole
2-[4-chloro-3-(trifluoromethyl)anilino]benzoxazole
2-[4-fluoro-3-(trifluoromethyl)anilino]benzoxazole
2-[N-(n-butyl)-4-chloro-3-(trifluoromethyl)anilino]benzoxazole
2-[N-carboxymethyl-4-chloro-3-(trifluoromethyl)anilino]benzoxazole
2-(2,4-difluoroanilino)benzoxazole
2-[4-(trifluoromethyl)anilino]benzoxazole
2-[3,5-di(trifluoromethyl)anilino]benzoxazole
2-(4-phenylanilino)benzoxazole
2-[2-(trifluoromethyl)-5-nitroanilino]benzoxazole
2-(N-benzylanilino)benzoxazole
2-(3-carbethoxyanilino)benzoxazole
2-[2-fluoro-5-(trifluoromethyl)anilino]benzoxazole
2-[4-chloro-3-(trifluoromethyl-N-(3-dimethylamino-n-propyl)anilino]benzoxazole
2-[N-carbanilino-4-chloro-3-(trifluoromethyl)anilino]benzoxazole Useful compounds of this invention in which the substituent denominated as X in the above formula is hydrogen can be prepared by a single step synthesis utilizing 2-chlorobenzoxazole as a starting material. The 2-chlorobenzoxazole is reacted with a substituted aniline in which the substituents desired in the final product are present on the phenyl ring of the aniline. The reaction is carried out by adding the 2-chlorobenzoxazole to a suitable solvent and adding thereto dropwise the desired substituted aniline in a suitable solvent until the addition is complete. Then the reaction mixture is refluxed on a steam bath for approximately 16 hours, or until a solid precipitate has formed. Water is then added to the reaction mixture, and the solvent is removed by distillation. The remaining aqueous dispersion is filtered, and the filter cake is recrystallized from a suitable solvent system yielding the desired 2-(substitutedanilino)benzoxazole.

It was found in the synthesis of the compounds described in the paragraph next above that tetrahydrofuran is an eminently satisfactory solvent in which to conduct the reaction. Other suitable solvents which can be employed include acetone, dioxane, benzene, diethyl ether, ethyl acetate, and the like. It is desirable that the solvent which is utilized for conducting the reaction shall be one in which both of the reactants are soluble. In order to carry out the reaction as it is described herein it is also desirable that the solvent should be one in which the resulting reaction product is insoluble.

After the crude rection product is filtered from the aqueous medium, it is dried by conventional means in vacuo and then taken up in an appropriate solvent such as benzene. Other suitable solvents which can be employed for the recrystallization procedure include: acetone, methanol, and the like. The solvent used for dissolving the crude reaction product is heated to minimize the quantity needed to effect complete solution, and a sufficient amount of hexane, water, or other precipitating vehicle is added to the solution to produce the crystallization of the desired 2-(substitutedanilino)benzoxazole. The crystallization is accomplished with an indefinite amount of precipitating vehicle, and it is possible to gage this by observing the cloud which forms in the solution. The precipitate is filtered off.

The 2-chlorobenzoxazole used in the synthesis of the thus described 2-(substitutedanilino)benzoxazoles is readily available in commerce. Many of the substituted anilines which can be employed in the reaction are also available from commercial sources. Substituted anilines which are used in the synthesis of these compounds which are not readily available from commercial sources can be synthesized by methods well-known to those skilled in the art.

The method of preparing the compounds of this invention wherein the substituent X is hydrogen and either one or two or $R_1$, $R_2$, $R_3$, and $R_4$ are other than hydrogen will be further illustrated by the following examples.

EXAMPLE 1

Preparation of 2-[4-bromo-3-(trifluoromethyl)anilino]benzoxazole

To a solution of 15.4 g. (0.1 mole) of 2-chlorobenzoxazole in 250 ml. of tetrahydrofuran was added dropwise a solution of 24.0 g. (0.1 mole) of 4-bromo-3-(trifluoromethyl)aniline in 100 ml. of tetrahydrofuran with vigorous stirring. Following the addition, the reaction mixture was heated on a steam bath under reflux for 16 hours. The reaction mixture was then cooled to about 25° C., and about 500 ml. of water was added. The tetrahydrofuran solvent was removed from the reaction mixture by distillation under vacuum. Following the removal of the solvent the reaction mixture was cooled to about 25° C., and the precipitate was filtered off. The filter cake was dried, and the solid was taken up in warm acetone. The acetone solution was brought to room temperature, and about 300 ml. of water was added, resulting in the crystallization of the reaction product. The reaction product was dried, yielding 28.0 g. of 2-[4-bromo-3-(trifluoromethyl)anilino]benzoxazole, having a melting point of 211°-212° C.

Analysis: $C_{14}H_8OBrF_3$; mol. wt.: 357 Calculated: C: 47.08; H: 2.25; N: 7.87; Found: C: 47.33; H: 2.52; N: 7.81.

EXAMPLE 2

Preparation of 2-[4-chloro-3-(trifluoromethyl)anilino]benzoxazole

A solution of 2-chlorobenzoxazole (15.4 g., 0.1 mole) in 150 ml. of tetrahydrofuran was added dropwise to a solution of 4-chloro-3-(trifluoromethyl)aniline (18.6 g., 0.1 mole) in 200 ml. of tetrahydrofuran under reflux on a steam bath. Following this addition, the reaction was maintained under reflux for about 16 hours. The tetrahydrofuran solvent was removed by distillation under vacuum. The oily residue thus formed was solidified by the addition of about 100 ml. of water. The residue was dissolved in a minimum amount of warm acetone, and about 200 ml. of water was added to the solution to give a crystalline precipitate. This precipitate was filtered and dried, yielding 25 g. of 2-[4-chloro-3-(trifluoromethyl)anilino]benzoxazole having a melting point of 199°-200° C.

Analysis: $C_{14}H_8ClF_3N_2O$; mol. wt. 312.5 Calculated: C, 53.77; H, 2.57; N, 8.96 Found: C, 53.60; H, 2.51; N, 8.73

EXAMPLE 3

Preparation of 2-(2-fluoro-5-trifluoromethylanilino)benzoxazole

A solution of 2-chlorobenzoxazole (15.4 g., 0.1 mole) in 150 ml. of tetrahydrofuran was added dropwise to a solution of 2-fluoro-5-(trifluoromethyl)aniline in 200 ml. of refluxing tetrahydrofuran. Reflux of the reaction mixture was continued on a steam bath for 16 hours. The tetrahydrofuran solvent was then removed by distillation under vacuum. The oily residue was solidified by addition of approximately 100 ml. of water. The solid material was separated by filtration and was recrystallized from an acetone-water solvent mixture to give 2-[2-fluoro-5-(trifluoromethyl)anilino]benzoxazole having a melting point of 164°-165° C.

Analysis: $C_{14}H_8F_4N_2O$; mol. wt. 296.22 Calculated: C, 56.76; H, 2.72; N, 9.40 Found: C, 56.64; H, 2.81; N, 9.16

EXAMPLE 4

Preparation of 2-[4-fluoro-3-(trifluoromethyl)anilino]benzoxazole

To a solution of 17.9 g. (0.1 mole) of 4-fluoro-3-(trifluoromethyl)aniline in 200 ml. of tetrahydrofuran was added dropwise 15.4 g. (0.1 mole) of 2-chlorobenzoxazole in 150 ml. of tetrahydrofuran with vigorous agitation. Following the addition, the reaction mixture was heated on a steam bath under reflux for 16 hours. Then the tetrahydrofuran solvent was removed by distillation under vacuum, and 100 ml. of water was added to the residue. The residue was an oily liquid which solidified on the addition of the water. The residue was removed by filtration and dried in vacuo. The dried residue was dissolved in a minimum amount of warm acetone, and about 200 ml. of water was added to the solution, resulting in the crystallization of the reaction product. The precipitate was filtered and dried and 24.5 g. of 2-[4-fluoro-3-(trifluoromethyl)anilino]benzoxazole having a melting point of 190°-191° C. was recovered.

Analysis: $C_4H_8N_2OF_4$; mol. wt.: 296 Calculated: C, 56.76; H, 2.72; N, 9.56; Found: C, 56.78; H, 2.89; N, 9.35.

EXAMPLE 5

Preparation of 2-(2,4-dichloroanilino)benzoxazole

A solution of 2,4-dichloroaniline (16.2 g., 0.1 mole) in about 100 ml. of tetrahydrofuran was added dropwise to a solution of 2-chlorobenzoxazole (15.4 g., 0.1 mole) in about 200 ml. of tetrahydrofuran. The resulting reaction mixture was heated on a steam bath under reflux for about 16 hours. The reaction mixture was then cooled to about 25° C., and approximately 500 ml. of water was added. The tetrahydrofuran solvent was removed from the reaction mixture by distillation under vacuum. The precipitate formed was separated by filtration, was dried and then was dissolved in a minimum amount of warm benzene. About 200 ml. of hexane was added, resulting in crystallization of the reaction product. Subsequent recrystallization from the benzenehexane solvent system afforded 6.8 g. of 2-(2,4-dichloroanilino)benzoxazole having a melting point of 98°-99° C.

Analysis: $C_{13}H_8ClN_2O$; mol. wt. 279 Calculated: C, 55.93; H, 2.88; N, 10.03 Found: C, 55.92; H, 3.03; N, 9.99

EXAMPLE 6

Preparation of 2-(2,4-difluoroanilino)benzoxazole

To a solution of 15.4 g. (0.1 mole) of 2-chlorobenzoxazole in 200 ml. of tetrahydrofuran was added dropwise a solution of 12.9 g. (0.1 mole) of 2,4-difluoroaniline in 100 ml. of tetrahydrofuran with vigorous agitation. Following the addition, the reaction mixture was heated on a steam bath under reflux for 16 hours. The reaction mixture was cooled to about 25° C., and about 500 ml. of water added thereto. The tetrahydrofuran solvent was removed by distillation under vacuum. The precipitate which formed in the aqueous medium was removed by filtration and dried. The dried precipitate was dissolved in a minimum amount of warm benzene. About 200 ml. of hexane was added to the benzene solution to effect crystallization of the reaction product. The precipitate was filtered off and dried, yielding 18.3 g. of 2-(2,4-difluoroaniline)benzoxazole having a melting point of 115°–117° C.

Analysis: $C_{13}H_8F_2N_2O$; mol wt.: 246; Calculated: C: 63.41; H: 3.27; N: 11.38; Found: C: 63.29; H: 3.32; N: 11.40.

EXAMPLE 7

Preparation of 2-[3-(trifluoromethyl)anilino]benzoxazole

To a stirred solution of m-aminobenzotrifluoride (15.1 g., 0.1 mole) in 200 ml. of tetrahydrofuran under reflux was added dropwise a solution of 2-chlorobenzoxazole (15.3 g., 0.1 mole) in 150 ml. of tetrahydrofuran. The resulting solution was heated under reflux on a steam bath for 16 hours. The tetrahydrofuran was evaporated by distillation under vacuum, leaving an oily residue which solidified upon the addition of 100 ml. of water. The precipitate was separated by filtration, dried, and crystallized from an acetone-water solvent mixture to give 22 g. of 2-[3-(trifluoromethyl)anilino]-benzoxazole with a melting point of 193°–194° C.

Analysis: $C_{14}H_9F_3N_2O$; mol. wt.: 278 Calculated: C, 60.43; H, 3.25; N, 10.07 Found: C, 60.30; H, 3.23; N, 9.86

EXAMPLE 8

Preparation of 2-[4-(trifluoromethyl)anilino]benzoxazole

To a solution of 15.4 g. (0.1 mole) of 2-chlorobenzoxazole in 200 ml. of tetrahydrofuran was added dropwise a solution of 16.1 g. (0.1 mole) of p-aminobenzotrifluoride in 100 ml. of tetrahydrofuran with vigorous agitation. Following the addition, the reaction mixture was heated on a steam bath under reflux for 16 hours. Then the reaction mixture was cooled to about 25° C., and about 500 ml. of water was added. The tetrahydrofuran solvent was removed by distillation under vacuum, leaving an aqueous slurry of the reaction product. The solids were filtered off and dried. The dried residue was dissolved in a minimum amount of warm benzene. Then about 200 ml. of hexane was added to the benzene solution to crystallize the reaction product. The crystals were filtered off and dried, yielding 19.2 g. of 2-[4-trifluoromethyl)anilino]benzoxazole having a melting point of 180°–182° C.

Analysis: $C_{14}H_9F_3N_2O$; mol. wt.: 278; Calculated: C: 60.43; H: 3.26; N: 10.07; Found: C: 60.33; H: 3.26; N: 10.27.

EXAMPLE 9

Preparation of 2-[3,5-di(trifluoromethyl)anilino]benzoxazole

To a solution of 15.4 g. (0.1 mole) of 2-chlorobenzoxazole in 200 ml. of tetrahydrofuran was added a solution of 22.9 g. (0.1 mole) of 3,5-di(trifluoromethyl)aniline in 100 ml. of tetrahydrofuran with vigorous agitation. Following the addition, the reaction mixture was heated on a steam bath under reflux for 16 hours. The reaction mixture was cooled to about 25° C., and about 500 ml. of water was added thereto. The tetrahydrofuran solvent was removed by distillation under vacuum, leaving a slurry of the reaction product in water. The residue was filtered off and dried. The dried precipitate was dissolved in a minimum amount of warm benzene. Then about 200 ml. of hexane was added to the benzene solution, effecting a crystallization of the reaction product. The crystals were filtered off and dried, yielding 28.5 g. of 2-[3,5-di(trifluoromethyl)anilino]benzoxazole having a melting point of 178°–180° C.

Analysis: $C_{15}H_8F_6N_2O$; mol. wt.: 376; Calculated: C: 52.03; H: 2.33; N: 8.09; Found: C: 51.82; H, 2.31; N: 8.23.

EXAMPLE 10

Preparation of 2-[2-(trifluoromethyl)-5-nitroanilino]benzoxazole

To a solution of 15.4 g. (0.1 mole) of 2-chlorobenzoxazole in 200 ml. of tetrahydrofuran was added a solution of 20.6 g. (0.1 mole) of 2-amino-5-nitrobenzotrifluoride in 100 ml. of tetrahydrofuran with vigorous agitation. Following the addition, the reaction mixture was refluxed on a steam bath for 16 hours. Then the reaction mixture was cooled to about 25° C., and 500 ml. of water was added thereto. Next, the tetrahydrofuran solvent was removed by distillation under vacuum, leaving an aqueous slurry of the reaction product. As the reaction product was an oil, the water was removed by distillation under vacuum, leaving behind the oil which solidified on cooling to room temperature. The solids were dissolved in a minimum amount of warm acetone. About 200 ml. of hexane was then added to the acetone solution to effect a crystallization of the reaction product. The crystals were filtered off and dried, yielding 8.7 g. of 2-[2-(trifluoromethyl)-5-nitroanilino]benzoxazole having a melting point of 150°–152° C.

Analysis: $C_{14}H_8F_3N_3O_3$; mol. wt.: 323; Calculated: C: 52.01; H: 2.49; N: 12.99; Found: C: 51.90; H: 2.68; N: 12.97.

Preparation of 2-(3-carbethoxyanilino)benzoxazole

A solution of 2-chlorobenzoxazole (15.4 g., 0.1 mole) in about 200 ml. of tetrahydrofuran was added dropwise to a solution of ethyl m-aminobenzoate (16.5 g., 0.1 mole) in about 100 ml. of tetrahydrofuran. Following this addition, the reaction mixture was heated on a steam bath under reflux for about 16 hours. The reaction mixture was then cooled to about 25° C., and approximately 500 ml. of water was added. The tetrahydrofuran solvent was removed by distillation, in vacuo. The precipitate was separated by filtration, washed with an aqueous saturated sodium bicarbonate solution, and then dried. The dried solution was dissolved in a minimal amount of ethyl acetate, and about 200 ml. of hexane was added. The crystalline product was separated by filtration to give 17.6 g. of 2-(3-carbethoxyanilino)benzoxazole with a melting point of 168°–170° C.

Analysis: $C_{16}H_{14}N_2O_3$; mol. wt. 282 Calculated: C, 68.07; H, 5.00; N, 9.92 Found: C, 68.03; H, 5.19; N, 10.01

EXAMPLE 12

Preparation of 2-(4-phenylanilino)benzoxazole

To a solution of 15.4 g. (0.1 mole) of 2-chlorobenzoxazole in 200 ml. of tetrahydrofuran was added dropwise a solution of 16.9 g. (0.1 mole) of p-aminodiphenyl in 100 ml. of tetrahydrofuran with vigorous agitation. Following the addition, the reaction mixture was heated on a steam bath under reflux for 16 hours. The tetrahydrofuran solvent was then removed by distillation under vacuum. The residue which resulted was the hydrochloride salt of the reaction product. The dried residue was treated with a 5 percent solution of sodium bicarbonate to remove the hydrochloride and effect the isolation of the crude 2-(4-phenylanilino)benzoxazole. The crude compound was dissolved in a minimum amount of warm acetone. About 200 ml. of hexane was added to the acetone solution, resulting in the appearance of crystals in the solution. The crystals were filtered off and dried, yielding 3.8 g. of 2-(4-phenylanilino)benzoxazole having a melting point of 212°–214° C. A second recrystallization from the acetone-hexane system as described above yielded 2.5 g. of crystalline 2-(4-phenylanilino)benzoxazole having a melting point of 213°–214° C.

Analysis: $C_{19}H_{14}N_2O$; mol. wt.: 286; Calculated: C: 79.70; H: 4.93; N: 9.78; Found: C: 79.87; H: 4.93; N: 9.80.

The novel compounds of this invention, wherein X in the heretofore detailed structural formula is a substituent other than hydrogen, can be prepared in either of two processes.

The first process accommodates those substituents which can be attached to the nitrogen of the aniline compound, either with or without substituents other than hydrogen on the phenyl ring of the aniline, without impairing the reactivity of the remaining H on the nitrogen of the aniline. Such compounds can be reacted with 2-chlorobenzoxazole, un-, mono- or disubstituted on the phenyl ring by following the general procedure outlined below.

A solution of the N-substituted-(un-, mono- or disubstituted)aniline in a suitable solvent, is added dropwise to a solution of 2-chlorobenzoxazole(un-, mono- or disubstituted on the phenyl ring) in a suitable solvent. Dioxane is a particularly useful solvent for both reactants. Other solvents which can be employed are tetrahydrofuran, acetone, diethyl ether, ethyl acetate, and the like. Then the reaction mixture is refluxed on a steam bath for approximately 16 hours, or until a reaction product has formed. Water is then added to the reaction mixture, and the solvent is removed by distillation in vacuo. The crude product in the resulting aqueous slurry is washed with an aqueous saturated sodium bicarbonate solution and either extracted with a suitable solvent such as diethyl ether, distilled and recrystallized or isolated by conventional chromatographic procedures. Other suitable partitioning solvents for extracting the reaction product from the crude mixture are chloroform, ethyl acetate, benzene, methylene chloride, and the like.

The following examples illustrate the preparation of certain anilinobenzoxazoles of this invention.

EXAMPLE 13

Preparation of 2-(N-benzylanilino)benzoxazole

A solution of N-benzylaniline (18.3 g., 0.1 mole) in about 100 ml. of dioxane was added dropwise to a solution of 2-chlorobenzoxazole (15.4 g., 0.1 mole) in about 200 ml. of dioxane. The resulting reaction mixture was heated on a steam bath under reflux for about 16 hours. The dioxane solvent was removed from the reaction mixture by distillation under vacuum. The crude product obtained was washed with a saturated sodium bicarbonate solution and then was extracted with diethyl ether. Distillation of the ether solution under vacuum afforded 23 grams of crude reaction product. The crude material was chromatographed over a column of Grace-Davidson silica gel prepared from a benzene slurry, and eluted with a benzene-chloroform-ethanol solvent system, in a ratio of 25:24:1. The chromatographic separation yielded 17.5 g. of 2-(N-benzylanilino)benzoxazole having a melting point of 60°–62° C.

Analysis: $C_{20}H_{16}N_2O$; mol. wt. 300 Calculated: C, 79.98; H, 5.37; N, 9.33 Found: C, 79.74; H, 5.55; N, 9.40

A preferred chromatographic material which was used for absorbing substituted 2-anilinobenzoxazoles is silica gel.

Eluting solvents found to be effective include benzene, ethyl acetate, methanol, chloroform, ethanol combinations of the aforementioned solvents, and the like.

EXAMPLE 14

Preparation of 2-[N-(n-butyl)-4-chloro-3-(trifluoromethyl)anilino]benzoxazole

A solution of N-(n-butyl)-4-chloro-3-(trifluoromethyl)aniline (26.3 g., 0.1046 mole) in about 100 ml. of dioxane was added dropwise to a solution of 2-chlorobenzoxazole (16.0 g., 0.1046 mole) in about 200 ml. of dioxane. The resulting reaction mixture was heated on a steam bath under reflux for about 16 hours. The reaction mixture was then cooled to about 25° C., and approximately 500 ml. of water was added. The dioxane solvent was removed from the reaction mixture by distillation in vacuo. The crude product was washed with an aqueous saturated sodium bicarbonate solution and extracted with diethyl ether. The ether solution was distilled to give 25.4 g. of 2-[N-(n-butyl)-4-chloro-3-(trifluoromethyl)anilino]benzoxazole having a boiling point of 166°–168° C./0.3 mm.

Analysis: $C_{18}H_{16}ClF_3N_2O$; mol. wt. 368.5 Calculated: C, 58.62; H, 4.37; N, 7.60 Found: C, 58.90; H, 4.48; N, 7.79

The N-(n-butyl)-4-chloro-3-(trifluoromethyl)aniline used for Example 16 above was prepared in the following manner:

Benzoyl chloride (140.5 g., 1.0 mole) was added dropwise with stirring to a solution of p-chloro-m-(trifluoromethyl)aniline (181.5 g., 1.0 mole) and pyridine (79 g., 1.0 mole) in two liters of dry benzene. Although the reaction was heated initially, the addition of benzoyl chloride generated sufficient heat to maintain reflux conditions during the addition. The reaction mixture was stirred overnight at room temperature and then was heated under reflux for 2 hours. After being cooled to about 25° C., the reaction product was washed successively with 6 N hydrochloric acid and saturated aqueous sodium bicarbonate solution, was dried over magnesium sulfate and was filtered. The filtrate was evaporated by distillation in vacuo, and the residue was crystallized from a benzene-hexane solvent to give two grams of 4'-chloro-3'-(trifluoromethyl)benzanilide, having a melting point of 130°-131° C.

This benzanilide (59.9 g., 0.2 mole) in about 300 ml. of dioxane was added dropwise with stirring to a solution of sodium hydride (50% in oil, 10.1 g., 0.22 mole) in about 250 ml. of dioxane in a flame-dried aparatus under a nitrogen atmosphere. The reaction was heated under reflux for two hours and then was cooled to room temperature for the dropwise addition of a solution of N-butyl bromide (37.05 g., 0.22 mole) in about 250 ml. of dioxane. The resulting reaction mixture was heated under reflux for 165 hours. The dioxane solvent was evaporated by distillation under vacuum. The crude product was dissolved in diethyl ether; the ether solution was washed successively with water and 3 N hydrochloric acid, was dried over magnesium sulfate and was filtered. The filtrate was distilled using a Vigreux column to give 37.6 g. of N-(n-butyl)-4'-chloro-3'-(trifluoromethyl)-benzanilide, having a boiling point of 177°-180° C./1.4 mm.

Hydrolysis of this N-(n-butyl)benzanilide (33 g., 0.093 mole) was accomplished by adding it to a solution of sodium hydroxide (10.8 g., 0.372 mole) in 200 ml. of water and 100 ml. of ethanol. The resulting solution was heated under reflux for 20 hours. The ethanol was then removed by distillation under vacuum. The remaining basic solution was extracted with diethyl ether; the ether extract was dried over magnesium sulfate and filtered. The filtrate was evaporated to dryness by distillation under vacuum. The crude product obtained was purified by addition of 6 N hydrochloric acid and separation of the water-insoluble salts thus formed. The acidic solution was then made basic by the addition of an aqueous 10% sodium hydroxide solution. The product was again extracted with ether and dried, as described above, to give 16.9 g. of N-(n-butyl)-4-chloro-3-(trifluoromethyl)aniline.

Other N-substituted anilines can be prepared in a similar manner. Methods for preparing phenyl ring substituted anilines are well known to chemists skilled in the art.

The second process which can be employed to prepare substituted 2-anilinobenzoxazoles wherein there is a substituent other than hydrogen on the N of the anilino moiety proceeds as follows:

The anilinobenzoxazole compound containing all of the substitutions desired on the phenyl ring, but with no substitution on the nitrogen of the anilino moiety is prepared by one of the procedures hereinbefore described. When the moiety which is desired on the nitrogen of the anilino moiety is contained in a molecule wherein there is a reactive substituent which will react directly with the hydrogen on the nitrogen, the desired compound can be prepared by a single addition-replacement reaction in a suitable solvent, such as one of those described hereinbefore. Refluxing the reaction mixture from 2 to 16 hours will complete the addition. The solvent is removed by distillation in vacuo, and the reaction product is recrystallized from a solvent mixture such as acetone-hexane, or one of those described hereinbefore.

The following example illustrates the preparation of a compound of this general procedure.

EXAMPLE 15

Preparation of 2-[N-(carbanilino)-4-chloro-3-(trifluoromethyl)anilino]-benzoxazole A solution of phenyl isocyanate (4.8 g., 0.04 mole) in 20 ml. of tetrahydrofuran was added dropwise with stirring to a mixture of 2-(4-chloro-3-trifluoromethylanilino)benzoxazole (12.5 g., 0.04 mole) in 100 ml. of tetrahydrofuran. The resulting mixture was heated under reflux for two hours.

The tetrahydrofuran solvent was then removed by distillation under vacuum. The solid residue was recrystallized from an acetone-hexane solvent mixture to give 14.0 g. of 2-[N-(carbanilino)-4-chloro-3-(trifluoromethyl)anilino]benzoxazole having a melting point of 142-144° C.

Analysis: $C_{21}H_{13}ClF_3N_3O_2$; mol. wt. 431.5 Calculated: C, 58.40; H, 3.03; N, 9.73 Found: C, 58.54; H, 3.14; N, 9.42

The preparation of an N-substituted anilinobenzoxazole wherein the substituent to be attached to the nitrogen is not readily available in a moiety which can be reacted directly as described above, can be accomplished by adding the appropriate anilinobenzoxazole to a solution of sodium hydride in a dry solvent, such as dioxane or one of those described hereinbefore. The reaction mixture is refluxed for about two hours, and after cooling a halogenated derivative of the desired substitution moiety is added dropwise in a dry solvent. Then the reaction mixture is refluxed for about five hours to complete the reaction. The solvent is then removed by distillation under vacuum. The residue contains the crude final product or a derivative thereof, such as an ester, which can then be converted to the crude product by procedures well known in the art. The crude product is purified by chromatography over a suitable adsorbent, such as silica gel, or recrystallized from a suitable solvent, such as benzene or the like, described hereinbefore.

The general procedure outlined above is illustrated by the examples below.

EXAMPLE 16

Preparation of 2-[N-carboxymethyl-4-chloro-3-(trifluoromethyl)anilino]benzoxazole A solution of sodium hydride (50% in oil, 2.0 g., 0.4 mole) in 50 ml. of dioxane was placed in a flame-dried apparatus under a nitrogen atmosphere. To this solution was added dropwise with a stirring a solution of 2-[4-chloro-3-(trifluoromethyl)anilino]benzoxazole (12.5 g., 0.04 mole, see Example 7) in 200 ml. of dioxane. The resulting reaction mixture was heated under reflux for two hours and then was cooled before the dropwise addition of a solution of ethyl bromoacetate (7.4 g., 0.044 mole) in 25 ml. of dioxane. The resulting solution was heated under reflux for five hours. The dioxane solvent was then removed by distillation under vacuum to give the crude ethyl ester of the N-carboxymethyl derivative.

The crude ester thus obtained was taken into a solution consisting of 100 ml. of ethanol and 200 ml. of 15% potassium hydroxide in water and was heated under reflux for about five hours. The ethanol was removed by distillation under vacuum. The potassium hydroxide solution remaining was extracted with diethyl ether, was made acidic by addition of concentrated hydrochloric acid, and then was re-extracted with ether. This latter ether extract was evaporated by distillation under vacuum to give 2-[N-carboxymethyl-4-chloro3-(trifluoromethyl)anilino]benzoxazole. The product was dissolved in a minimal amount of benzene, and an appropriate amount of higher aromatic naphtha was added to effect recrystallization. The melting point of the product was 141°-144° C.

Analysis: $C_{16}H_{10}ClF_3N_2O_3$; mol. wt. 386.5 Calculated: C, 51.83; H, 2.71; N, 7.55 Found: C, 51.96; H, 2.76; N, 7.44

EXAMPLE 17

Preparation of
2-[4-chloro-3-trifluoromethyl-N-(3-dimethylamino-n-propyl)anilino]benzoxazole hydrochloride A solution of 2-[4-chloro-3-(trifluoromethylanilino]-benzoxazole (12.5 g., 0.04 mole) in 200 ml. of dioxane was added dropwise with stirring to a soluton of sodium hydride (50% in oil, 2.0 g., 0.04 mole) in 50 ml. of dioxane in a flame-dried apparatus under a nitrogen atmosphere. The reaction mixture was heated under reflux for two hours and then was cooled before the dropwise addition of a solution of dimethylaminopropyl chloride (5.4 g., 0.044 mole) in 25 ml. of dioxane. The resulting solution was heated under reflux for five hours. The dioxane solvent was removed by distillation in vacuo to give 18 g. of crude product.

This crude product was purified by chromatography over a column of silica gel prepared by ethyl acetate and eluted with an ethyl acetate-methanol solvent mixture (1:1 ratio). Further elution with methanol yielded 16.2 g. of 2-[4-chloro-3-trifluoromethyl-N-(3-dimethylamino-n-propyl)anilino]benzoxazole, which was converted to 9.2 g. of the hydrochloride salt, having a melting point of 116°-118° C.

Analysis: $C_{19}H_{20}Cl_2F_3N_3O$; mol. wt. 434 Calculated: C, 52.54; H, 4.64; N, 9.68 Found: C, 52.37; H, 4.75; N, 9.53

In each of the 17 examples described above, the structure of the compound synthesized was confirmed by nuclear magnetic resonance spectroscopy.

In a preferred embodiment of this invention, useful 2-(substitutedanilino)benzoxazoles are provided which are effective in suppressing the immune response in warm-blooded mammals. The immune response is generally accepted as the mechanism which is set into action when a foreign protein enters the tissues or cells. The body brings its defensive mechanisms into play to reject the foreign invader and protect the integrity of the tissue of cell type. An example of this immune response is illustrated by the rejection of organ transplants, such as kidneys, from another body other than an identical twin, or in skin grafts. Success in heart transplant cases is due in part, along with the skill of the surgeon, to an effective suppression of the immune response of the transplantee.

Certain in vivo tests have been developed to detect immunosuppressive activity in test compounds. The immunosuppressive activity of the useful substituted anilinobenzoxazoles of this invention is demonstrated by the suppression of the development of antibodies in Swiss mice to sheep red blood cells when the latter are injected intraperitoneally into the mice.

A modification of the procedure of Nathan, et. al. [Nathan, H. C.; Bieber, S.; Elion, G. B.; and Hitchings, G. H.; Proc. Soc. Exptl. Biol. Med., 107, 796 (1961)] was employed to determine immunosuppressive activity. Groups of five 20 g. Swiss mice were injected intraperitoneally with 0.2 ml. of 1:80 standardized suspensions of sheep red blood cells (approximately $5 \times 10^7$ cells/mouse). At 72, 48 and 24 hours before the red blood cell injections, test compounds there injected by the same route. Eight days after the red cell antigen injections, the mice were bled by cardiac puncture, and the sera from each five-mouse group was pooled. Antibody determinations were made on the serum pools by a hemagglutination pattern procedure, and comparisons were made between treated and control animals. The results were reported as the minimum levels (mg/kg × 3) of drug necessary to suppress the hemagglutination titer by a factor of four fold or greater from control titers.

Test compounds were dissolved or suspended in corn oil for the intraperitoneal injection.

The table below shows the immunosuppressive activity of representative 2-(substitutedanilino)benzoxazoles. The figures shown are mg. of test compound/kg. of body weight administered on each of three occasions as described hereinbefore (mg/kg × 3).

TABLE I

Immunosuppressive Activity of Representative 2-(Substitutedanilino)benzoxazoles

| Compound | Mg/Kg × 3 Effective in Producing Fourfold or Better Suppression in Hemagglutination Titer |
|---|---|
| 2-(2,4-dichloroanilino)benzoxazole | 12.5 |
| 2-(2,5-dichloroanilino)benzoxazole | 100 |
| 2-[4-chloro-3-(trifluoromethyl)-anilino]benzoxazole | 0.8 |
| 2-[2-(trifluoromethyl)anilino]-benzoxazole | 100 |
| 2-[3-(trifluoromethyl)anilino]-benzoxazole | 1.6 |
| 2-(3,4-dichloroanilino)benzoxazole | 3.1 |
| 2-[N-benzyl-3-(trifluoromethyl)anilino]- | >25 |
| 2-[4-chloro-3-(trifluoromethyl)-N-(n-butyl)anilino]benzoxazole | 12.5 |
| 2-[4-chloro-2-(trifluoromethyl)anilino]-benzoxazole | 100 |
| 2-[4-bromo-3-(trifluoromethyl)anilino]-benzoxazole | 0.4 |
| 2-[2-fluoro-5-(trifluoromethyl)anilino]-benzoxazole | 12.5 |
| 2-(2,3-dimethylanilino)benzoxazole | 25 |
| 2-[4-fluoro-3-(trifluoromethyl)anilino]-benzoxazole | 12.5 |
| 2-[4-bromo-2(trifluoromethyl)anilino]-benzoxazole | 100 |
| 2-[4-chloro-3-(trifluoromethyl)-N-methylanilino]benzoxazole | 25 |
| 2-(3-carbethoxyanilino)benzoxazole | 25 |
| 2-(4-carbethoxyanilino)benzoxazole | 25 |
| 2-(2,4-difluoroanilino)benzoxazole | 50 |
| 2-[4-trifluoromethyl)anilino]benzoxazole | 50 |
| 2-[3,5-di(trifluoromethyl)anilino]-benzoxazole | 25 |
| 2-(4-phenylanilino)benzoxazole | 25 |
| 2-(N-benzylanilino)benzoxazole | 25 |
| 2-[4-chloro-3-(trifluoromethyl)-N-benzyl-anilino]benzoxazole | 100 |
| 2-[4-chloro-3-(trifluoromethyl)-N-(carboxymethyl)anilino]benzoxazole | 12.5 |
| 2-[4-chloro-3-(trifluoromethyl)-N-(carbanilino]Benzoxazole | 25 |
| 2-[3-(methylsulfonyl)anilino]benzoxazole | 100 |
| 2-[3-(methylthio)anilino]benzoxazole | 100 |

In another embodiment of this invention a method is provided for suppressing the immune response in a mammal comprising administering to such mammal a compound of the formula

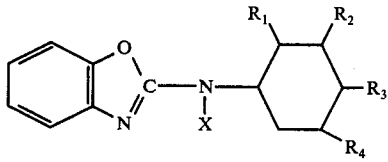

wherein,

X is hydrogen, $C_1$-$C_4$ alkyl, $C_1$-$C_3$ alkoxy, $C_1$-$C_3$ alkoxy $C_1$-$C_3$ alkyl, carboxy, carboxy $C_1$-$C_3$ alkyl, amino $C_1$-$C_3$ alkyl, mono-$C_1$-$C_3$ alkylamino $C_1$-$C_3$ alkyl, di-$C_1$-$C_3$ alkylamino $C_1$-$C_3$ alkyl, anilino $C_1$-$C_3$ alkyl, $C_1$-$C_3$ alkylthio, $C_1$-$C_3$ alkylsulfonyl, phenyl, phenyl $C_1$-$C_3$ alkyl, or carbanilino;

$R_1$, $R_2$, $R_3$, and $R_4$ are hydrogen, bromine, chlorine. fluorine, trifluoromethyl, carboxy, $C_1$-$C_3$ alkyl, $C_1$-$C_3$ alkoxy, carboxy C-$C_3$ alkyl, $C_1$-$C_3$ alkoxy $C_1$-$C_3$ alkyl, carb $C_1$-$C_3$ alkoxy, $C_1$-$C_3$ alkylthio, $C_1$-$C_3$ alkylsulfonyl, phenyl, or nitro, such that no more than one of $R_1$, $R_2$, $R_3$, and $R_4$ is nitro or phenyl, and no more than two of $R_1$, $R_2$, $R_3$, and $R_4$ are other than hydrogen.

In addition to the novel 2-(substitutedanilino) benzoxazoles described hereinbefore, and which are included within the class of compounds coming within the scope of such method, 2-anilinobenzoxazole, 2-(monobromo-, monochloro-, and monofluorosubstitutedanilino)benzoxazoles, 2-(mono $C_1$-$C_3$ alkyl substitutedanilino-benzoxazoles, 2-(mononitrosubstitutedanilino)benzoxazole and 2-[1-(or 2-)naphthylamino] benzoxazole are effective in suppressing the immune response in warm-blooded mammals. TABLE Ia, below, shows the effectiveness of these latter compounds.

TABLE Ia

Immuno Suppressive Activity of Additional 2-(Substitutedanilino)benzoxazoles

| Compound | Mg/Kg × 3 Effective in Producing Four-fold or Better Suppression in Hemagglutination Titer |
|---|---|
| 2-anilinobenzoxazole | 100 |
| 2-(4-chloroanilino)benzoxazole | 50 |
| 2-(2-chloroanilino)benzoxazole | 100 |
| 2-(3-chloroanilino)benzoxazole | 100 |
| 2-(3-methylanilino)benzoxazole | 100 |
| 2-(1-naphthyamino)benzoxazole | 25 |
| 2-(4-nitroanilino)benzoxazole | 100 |
| 2-(3-nitroanilino)benzoxazole | 100 |

This, it can be seen from Table I and TABLE Ia that the 2-(substitutedanilino)benzoxazoles coming within the scope of the class of compounds described by the generic formula detailed next above are effective immuno suppressants. All of these compounds can be prepared following the general procedure as outlined hereinbefore in Examples 1 through 12.

A preferred method of administering the immunosuppressive agents of this invention comprises parenterally injecting the compounds into warm-blooded mammals either intraperitoneally, intradermally, subcutaneously or intramuscularly. Pharmaceutically acceptable parenteral formulations can be prepared by methods commonly known and available in the art.

Furthermore, the active compounds of this invention are effective in suppressing the immune response when administered orally to swiss mice. For example, 2-[4-chloro-3-(trifluoromethyl)anilino]benzoxazole administered to swiss mice by gavage in a corn oil suspension in an amount of 100 mg/kg at 72, 48, and 24 hours preceding the infection of sheep red blood cells, as described above, effectively suppressed the immune response.

Preferred pharmaceutical formulations for oral administration to warm-blooded mammals comprise capsules and tablets, and the preparation of these dosage forms is well known to those skilled in the art.

In another embodiment of this invention, some of the useful compounds of this invention are antifertility agents. These substituted 2-anilinobenzoxazoles are of the formula:

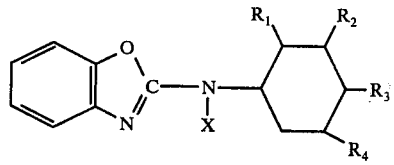

wherein,

X is hydrogen.

$R_1$, $R_2$, and $R_4$ are hydrogen, bromine, chlorine, flourine, methyl, trifluoromethyl, methoxy, or nitro, such that only one of $R_1$, $R_2$, and $R_4$ is nitro, and no more than two of $R_1$, $R_2$ and $R_4$ are other than hydrogen;

$R_3$ is hydrogen, bromine, chlorine, fluorine, methyl, trifluoromethyl, methoxy, nitro, or phenyl, such that $R_3$ is nitro only, when $R_1$, $R_2$, and $R_4$ are other than nitro, and $R_3$ is hydrogen only when one or more of $R_1$, $R_2$, and $R_4$ are other than hydrogen; and with the proviso that no more than two of $R_1$, $R_2$, $R_3$ and $R_4$ are other than hydrogen.

The antifertility activity of the appropriate 2-(substitutedanilino)benzoxazoles is demonstrated by administering to a group of virgin young adult female rats weighing 200-300 grams the active compound for five days prior to being exposed to adult male rats as studs, and for the following 15 days during which time the males and females are housed together. A control group is fed and housed in the same manner, At the end of the 15 day cohabitation period the administration of the compound is terminated, and the males are removed from the groups. Seven days later the females are weighed and necropsied. The number of inplantation sites, resorbtion sites and viable fetuses are determined for both the test and control groups.

One measure of antifertility activity is indicated by:

$$\text{Ratio} \frac{\text{No. of animals with implantation sites}}{\text{No. of animals in test group.}}$$

A ratio of 0/5 or 1/5 is considered an indication of activity.

Other important considerations are the average number of viable fetuses and the total number of resorbtion sides, and the activity can also be indicated by a combination of these parameters. A compound having estrogenic antifertility activity will generally demonstrate a ratio of 0/5 or 1/5 with no viable fetuses or resorbtion sites, indicating no pregnancy was established as no conception occurred. On the other hand, an abortafacient antifertility activity will generally be indicated by a high ratio of 4/5 or 5/5 with a zero, or small average number of viable fetuses and a relatively high number of resorbtion sites.

The antifertility activity of the useful substituted 2-anilinobenzoxazoles described immediately above was demonstrated by daily injecting the test compound, dissolved or suspended in corn oil, subcutaneously in amounts of from about 0.1 to about 5.0 mg. The administration was continued for 20 days, with the male and female rats together for the last 15 days of the injections. Seven days after the last injection the females were weighed and necropsied. The table below shows the antifertility activity of five representative 2-(substitutedanilino)benzoxazoles.

These useful 2-(substitutedanilino)benzoxazoles are conveniently fed to chickens in a feed component.

Novel compositions are provided in this invention which comprise a 2-(substitutedanilino)benzoxazole, such as one of those described next above, intimately admixed with an edible, inert, solid carrier or diluent to provide a premix, or a medicated feed concentrate or supplement. An inert edible carrier or diluent is one that

TABLE II

| | Antifertility Activity of Five Representative 2-(Substitutedanilino)benzoxazoles | | | | | |
|---|---|---|---|---|---|---|
| 1 Compound | 2 Quantity Administered Daily for 20 Days, mg. | 3 Ratio$^a$ of Pregnancies Control Group | 4 Ratio$^a$ of Pregnancies Test Group | 5 Average No. of Viable Fetuses/Rat Control Group | 6 Average No. of Viable Fetuses/Rat Test Group | 7 Total No. of Resorbtion Sites in Test Group |
| 2-[4-Chloro-3-(trifluoro-methyl)anilino]benzoxazole | 0.5 | 5/5 | 5/5 | 12 | 3 | 46 |
| | 1.0 | 5/5 | 4/5 | 12 | 3 | 36 |
| | 5.0 | 5/5 | 12 | | 0 | 49 |
| 2-[3-(trifluoromethyl)-anilino]benzoxazole | 0.1 | 4/5 | 4/5 | 13 | 8 | 18 |
| | 0.5 | 4/5 | 4/5 | 13 | 3 | 38 |
| | 0.5 | 4/5 | 0/5 | 12 | 0 | 0 |
| | 1.0 | 4/5 | 3/5 | 12 | 0 | 33 |
| | 2.0 | 5/5 | 5/5 | 12 | 4 | 34 |
| | 5.0 | 4/5 | 3/5 | 12 | 3 | 13 |
| 2-[4-Bromo-3-(trifluoro-methyl)anilino]benzoxazole | 0.5 | 5/5 | 2/5 | 12 | 0 | 22 |
| | 1.0 | 5/5 | 5/5 | 10 | 0 | 55 |
| | 3.0 | 4/5 | 3/5 | 12 | 4 | 28 |
| | 5.0 | 4/5 | 2/3 | 12 | 3 | 15 |
| 2-[4-Fluoro-3-(trifluoro-methyl)anilino]benzoxazole | 0.5 | 5/5 | 5/5 | 12 | 0 | 55 |
| | 1.0 | 5/5 | 4/5 | 10 | 0 | 38 |
| | 3.0 | 4/5 | 5/5 | 12 | 0 | 54 |
| | 5.0 | 5/5 | 3/5 | 10 | 1 | 34 |
| 2-(3,4-dimethylanilino)-benzoxazole | 2.0 | 4/5 | 5/5 | 13 | 12 | 5 |
| | 5.0 | 4/5 | 3/5 | 13 | 6 | 23 |

$^a$Ratio = $\frac{\text{No. of animals with implantation sites}}{\text{No. of animals in test group.}}$ A preferred method of administering the antifertility agents of this invention comprises parenterally injecting into warm-blooded mammals a fertility controlling amount of the compound intraperitoneally, intradermally, subcutaneously or intramuscularly. Pharmaceutically acceptable parenteral formulations can be prepared by methods commonly known and available in the art.

In still another embodiment of this invention, certain 2-(substitutedanilino)benzoxazoles, when administered orally, are effective in improving weight gains and reducing gross lesions in chickens exposed to Marek's disease. These compounds are exemplified by the formula

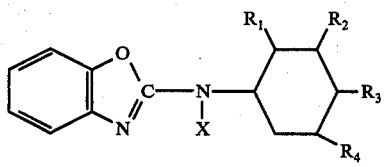

wherein,

X is hydrogen;

$R_1$, $R_2$, and $R_4$ are hydrogen, bromine, fluorine, methyl, trifluoromethyl, or nitro, such that only one or $R_1$ and $R_2$ is other than hydrogen, and no more than two or $R_1$, $R_2$, and $R_4$ are other than hydrogen on the same molecule; and $R_3$ is hydrogen, bromine, fluorine, methyl, trifluoromethyl, phenyl, or nitro, such that $R_3$ is hydrogen only when two of $R_1$, $R_2$, and $R_4$ are other than hydrogen; and with the proviso that there is no more than one nitro and no more than two of $R_1$, $R_2$, $R_3$, and $R_4$ and other than hydrogen.

does not react with the active ingredient, and can be either a nutritive or non-nutritive material compatible with animal feed.

The preferred compositions of this invention are feed premixes in which a 2-(substitutedanilino)benzoxazole is present in relatively large amounts, and which are suitable for addition to chicken feed rations either directly or after an intermediate dilution or blending step. Examples or carriers or diluents which are suitable for such compositions are soybean meal, soybean grits, soybean mill run, alfalfa granules, wheat middlings, distillers' dried grains, corn meal, corn cob meal, citrus pulp meal, fermentation residues, sugar beet pulp meal, exfoliated hydrobiotite, attapulgus clay, kaolin clay, talc, ground limestone, and the like. Preferred carriers are soybean products, such as soybean grits and alfalfa products, such as alfalfa granules.

The compositions can be prepared by intimately admixing the appropriate 2-(substitutedanilino)benzoxazole with the desired carrier or diluent. This operation can be accomplished by adding the carrier or diluent to any one of the many varieties of feed mixers commonly exployed in preparing multiple component feed rations; ribbon blenders, vertical mixers, paddle mixers, tumbling cones, twin-shell blenders, and the like, starting the mixer and adding the appropriate 2-(substitutedanilino)benzoxazole thereto as a finely divided powder. The operation of the mixer is continued until an homogeneous blend is produced, the time varying with the type of mixer utilized, but within the scope of knowledge of those skilled in preparing feed mixes. It may be desirable to add from about 0.1 to about 5.0 percent, preferably from about 1.0 to about 2.0 percent of an oil, such as mineral oil or a suitable vegetable oil, such as soybean oil, to the mix to reduce the dust and promote the adherence of the 2-(substitutedanilino)benzoxazole to the carrier particles.

Alternatively, the premix composition can be prepared by dissolving or suspending the appropriate 2-(substitutedanilino)benzoxazole in an edible liquid such as propylene glycol, glycerin, soybean oil, molasses, wood sugar concentrate, or similar suitable vehicle and spraying the resulting solution or dispersion onto the carrier or diluent in a mixer such as one of those enumerated above. By selecting the proper carrier or diluent, and altering the ratio of carrier to active ingredient, compositions of any desired concentration can be obtained.

Feed premixes can be formulated so that the total active ingredient is present within the range of 2 to 80 percent by weight, and the carrier or diluent respresents from 20 to 98 percent by weight of the premix. However, the preferred ratio is from 20 to 40 percent active ingredient and 60 to 80 percent carrier or diluent. An especially preferred composition contains about 33 percent active ingredient and about 67 percent carrier or diluent.

Premixes prepared as described above can be further diluted with feedstuff ingredients such as corn meal, soybean meal, vitamin premixes, minerals, mineral premixes, and the like, before being incorporated into the chicken feed ration, or the premix can be added directly to the finished chicken feed ration. In either case, a uniform homogeneous admixture can be prepared by employing suitable mixing equipment, as denoted above. A finished feed ration is one that contains a source of protein, carbohydrate, fat, vitamins, minerals, and other nutritional factors, providing the chicken with a balanced diet designed to promote healthy growth.

In this specification the term "chicken feed ration" means a finished feed ration, a feed concentrate or feed supplement, or a feed premix. A finished feed ration is described in more detail in the paragraph next above. The terms feed concentrate and feed supplement are sometimes interchangeable, but are generally agreed to describe an intermediate mixture of feed ingredients comprising more than a premix but less than a finished feed. A feed premix is described in greater detail hereinbefore.

In the program for improving weight gains and reducing gross lesions in chickens exposed to Marek's disease, relatively low levels of an appropriate 2-(substitutedanilino)benzoxazole of this invention administered in the feed are sufficient to produce a statistically significant increase in the weight gains and a reduced incidence of gross lesions of such chickens. The active ingredient is administered to chickens in an amount equal to about 0.005 to about 0.03 percent by weight of the daily feed intake. The preferred range is from about 0.01 to about 0.02 percent with the optimum results being obtained when about 0.016 percent or 0.33 lbs/ton of active ingredient is incorporated into the chicken feed. Because the severity of Marek's disease is dependent on many factors, such as the season, the weather, the general hygiene of the growing quarters, genetic resistance present in the chickens, and others, the actual amount of active ingredient required to meet the particular circumstances of each situation will vary, and consequently the most advantageous dosage level will vary with the individual flock.

Chickens appear to have some natural resistance to Marek's disease, since not all chickens exposed to the disease contract the infection. The daily oral administration of the 2-(substitutedanilino)benzoxazoles of this invention is a prophylactic measure, as the number of chickens which contract the disease after being exposed to the Marek's virus is lessened, and consequently, the average weight gains are improved and the number of chickens rejected for gross lesions at the processing plant is reduced. Thus, the active compounds of this invention are useful in the prophylaxis of Marek's disease.

In treating chickens according to the method preferred in one embodiment of the present invention, one day old chicks are placed on medicated feed containing an appropriate 2-(substitutedanilino)benzoxazole. This procedure is useful for both broilers and replacement stock for layer flocks. Broiler chickens are maintained on the medicated feed composition of this invention from the time of hatching until they are between five and six weeks of age. Replacement stock for layer flocks are maintained on the medicated feed for a minimum of 12 to 14 weeks.

An appropriate 2-(substitutedanilino)benzoxazole of the present invention is administered orally to chickens in a conventional chicken feed ration which can comprise the following ingredients: Meat and bonescrap, fish meal, poultry by-product meal, dehulled soybean oil meal, dehydrated alfalfa meal, corn meal, corn gluten meal, pulverized oats, ground barley, wheat middlings, dried grain solubles, distillers' dried grains, dried whey solubles, molasses, molasses solubles, animal fat, vitamin $B_{12}$, vitamin E, vitamin A palmitate, vitamin D, riboflavin, niacin, menadione sodium bisulfite, calcium pantothenate, methionine hydroxy analogue, choline chloride, butylated hydroxytoluene, calcium carbonate, dicalcium phosphate, salt, calcium iodate, manganese oxide, zinc oxide, cobalt hydroxide, cobalt carbonate, and the like.

A medicated feed composition is prepared by adding the appropriate 2-(substitutedanilino)benzoxazole of this invention to the finished feed in an amount constituting about 0.016 percent by weight of the final mixture. The ingredients are thoroughly admixed to prepare the feed given to the chickens.

The following examples further illustrate the compositions of this invention.

EXAMPLE 18

Chicken feed premixes having the following compositions are prepared by intimately admixing an appropriate 2-(substitutedanilino)benzoxazole with the particular edible solid diluent. Approximately 1.0 percent by weight of light mineral oil was added to the mixture.

| | Ingredients | Parts by Weight |
|---|---|---|
| (A) | 2-[4-(Trifluoromethyl)anilino]-benzoxazole | 33 |
| | Alfalfa granules | 66 |
| | LIght mineral oil | 1 |
| (B) | 2-[3,5-Di(trifluoromethyl)anilino]-benzoxazole | 25 |
| | Soybean grits | 74 |
| | Light mineral oil | 1 |
| (C) | 2-[2-(Trifluoromethyl)-5-nitroanilino]-benzoxazole | 30 |
| | Soybean mill run | 69 |
| | LIght mineral oil | 1 |
| (D) | 2-[4-Bromo-3-(trifluoromethyl)anilino]-benzoxazole | 33 |
| | Corn meal | 66 |
| | Light mineral oil | 1 |
| (E) | 2-(2,4-Difluoroanilino)benzoxazole | 40 |

-continued

| Ingredients | | Parts by Weight |
|---|---|---|
| | Distillers' dried grains | 59 |
| | Light mineral oil | 1 |
| (F) | 2-(4-Phenylanilino)benzoxazole | 15 |
| | Wheat shorts | 84 |
| | Light mineral oil | 1 |
| (G) | 2-(3,4-Dimethylanilino)benzoxazole | 60 |
| | Molasses solubles | 39 |
| | Light mineral oil | 1 |
| (H) | 2-[4-Fluoro-3-(trifluoromethyl)anilino]-benzoxazole | 50 |
| | Soybean feed | 49 |
| | Light mineral oil | 1 |

EXAMPLE 19

A medicated starter feed for broiler chicks is prepared by mixing about 0.016 percent by weight (0.33 lb./ton) of 2-[4-(trifluoromethyl)anilino]benzoxazole, contained in a premix as described as (A) in Example 9, above, into a typical starter ration having the following composition:

| Broiler Starter | | |
|---|---|---|
| Ingredients | Percent | Lbs./ton |
| Corn, yellow, ground | 58.0 | 1,160 |
| Soybean oil meal, solvent extracted dehulled (50 percent) | 18.0 | 360 |
| Corn gluten meal (60 percent) | 5.0 | 100 |
| Distillers' dried solubles, corn | 5.0 | 100 |
| Fish meal with solubles | 5.0 | 100 |
| Meat scraps (55 percent) | 4.0 | 80 |
| Alfalfa meal, dehydrared (17 percent) | 2.0 | 40 |
| Animal fat, beef tallow | 1.0 | 20 |
| Dicalcium phosphate, feed grade | 0.6 | 12 |
| Calcium carbonate (ground limestone) | 0.5 | 10 |
| Salt (NaCl) | 0.3 | 6 |
| Trace mineral premix AN-01 (1.05)[1] | 0.1 | 2 |
| Vitamin premix CK-01 (1.02)[2] | 0.5 | 10 |
| Total | 100.0 | 2,000 |

[1]Trace mineral premix provides per pound complete feed: manganese, 30.4 mg; zinc, 34.0 mg.; iron, 7.7 mg.; copper, 0.8 mg.; and iodine, 0.4 mg.
[2]Vitamin premix provides per pound complete feed: vitamin A, 2250 IU; vitamin $D_3$, 600 ICU; vitamin E, 51U; menadione sodium bisulfite, 0.5 mg,; riboflavin, 2 mg.; niacin, 18 mg.; pantothenic acid, 4.8 mg.; choline, 130 mg.; and vitamin $B_{12}$, 5 mcg.

At four weeks of age, the broiler chicks are changed to a suitable medicated feed prepared by mixing about 0.016 percent by weight of 2-[4-(trifluoromethyl)anilino]benzoxazole, contained in a premix as described as (A) in Example 9, above, into a typical finished ration having the following composition:

| Broiler Finisher | | |
|---|---|---|
| Ingredients | Percent | Lbs./ton |
| Corn, yellow, ground | 62.8 | 1,256 |
| Soybean oil meal, solvent extracted dehulled (50 percent) | 28.7 | 574 |
| Animal fat, beef tallow | 5.2 | 104 |
| Dicalcium phosphate, feed grade | 1.5 | 30 |
| Calcium carbonate (ground limestone) | 0.75 | 15 |
| Salt (NaCl) | 0.25 | 5 |
| Trace mineral premix AN-01 (1.05)[3] | 0.1 | 2 |
| Vitamin premix CK-01 (1.02)[4] | 0.5 | 10 |
| Methionine hydroxy analogue (90 percent) | 0.2 | 4 |
| Total | 100.0 | 2,000 |

[3]See 1 supra.
[4]See 2 supra.

EXAMPLE 20

To reduce the incidence of Marek's disease symptons in chickens destined to be layer stock, the chicks are started on a suitable medicated starter feed prepared by mixing about 0.016 percent by weight of an appropriate 2-(substitutedanilino)benzoxazole, in a premix such as those described as (A) through (H) in Example 0, above, into a typical starter ration having the following composition:

| Chick Starter (0 to 6 weeks) | | |
|---|---|---|
| Ingredients | Percent | Lbs./ton |
| Corn, yellow, ground | 55.0 | 1,100 |
| Wheat middlings | 10.0 | 200 |
| Soybean oil meal, solvent extracted dehulled (50 percent) | 19.0 | 380 |
| Meat scraps | 5.0 | 100 |
| Distillers' dried solubles, corn | 2.5 | 50 |
| Fish meal with solubles | 2.5 | 50 |
| Alfalfa meal, dehydrated (17 percent) | 2.2 | 44 |
| Whey, whole, dried | 1.5 | 30 |
| Dicalcium phosphate, feed grade | 0.5 | 10 |
| Calcium carbonate (ground limestone) | 0.75 | 15 |
| Salt (NaCl) | 0.25 | 5 |
| Trace mineral premix AN-01 (1.05)[5] | 0.1 | 2 |
| Vitamin premix CK-01 (1.02)[6] | 0.5 | 1 |
| Methionine hydroxy analogue (90 percent) | 0.6 | 0 |
| Total | 100.0 | 2,000 |

[5]See 1 supra.
[6]See 2 supra.

When chicks destined to be layers are about six weeks of age, the feed containing about 0.016 percent by weight of an appropriate 2-(substitutedanilino)benzoxazole, such as one of those described in the premixes (A) through (H) shown in Example 20, above, is changed to one having the following approximate formula:

| Pullet Grower (6 to 12-14 Weeks) | | |
|---|---|---|
| Ingredients | Percent | Lbs./ton |
| Corn, yellow, ground | 66.0 | 1,320 |
| Soybean oil meal, solvent extracted dehulled (50 percent) | 12.0 | 240. |
| Wheat middlings | 10.0 | 200 |
| Meat scraps | 5.0 | 100 |
| Alfalfa meal, dehydrated (17 percent) | 2.4 | 48 |
| Fish meal with solubles | 1.5 | 30 |
| Distillers' dried solubles, corn | 1.2 | 24 |
| Dicalcium phosphate, feed grade | 0.4 | 8 |
| Calcium carbonate (ground limestone) | 0.4 | 8 |
| Salt (NaCl) | 0.25 | 5 |
| Trace mineral premix AN-01 (1.05)[7] | 0.1 | 2 |
| Vitamin premix CK-01 (1.02)[8] | 0.5 | 10 |
| Methionine hydroxy analogue (90 percent) | 0.25 | 5 |
| Total | 100.0 | 2,000 |

[7]See 1 supra.
[8]See 2 supra.

Layer chickens are maintained on a medicated feed, such as that described above, until they are about 12 to 14 weeks of age, at which time the 2-(substitutedanilino)benzoxazole is withdrawn from the diet, and usually the feed ration is also changed.

EXAMPLE 21

These tests were run to determine the effect of the oral administration in the feed of 2-(substitutedanilino)-benzoxazoles on the development of Marek's disease infection in chickens. Feed premixes were prepared for each of the active ingredients in the test by admixing 33 parts by weight of the test compound, 66 parts by weight of alfalfa granules and 1 part by weight of light mineral oil. Each premix was then uniformly blended into a broiler starter feed, as described in Example 10, to provide the amount of active ingredient as shown in the table below. This medicated feed was fed to the chickens until they were four weeks of age. Then the feed formula was changed to that described as broiler finisher in Example 10, and the premix containing the active ingredient was admixed therewith to provide the proper amount of medication. At five and one-half weeks of age the medication was discontinued, and the chickens were maintained on the broiler finisher until they were eight weeks old, at which time they are sacrificed.

Infected control chickens were maintained in the same facilities as the treated chickens, receiving the same ration without medication. All chickens were injected intraperitoneally on the day of hatching with a 0.5 ml. dose of a $10^{-2}$ dilution of whole blood from chickens known to be infected with Marek's disease. The dilution of the blood was made with Hank's balanced salt solution.

At the end of the test, the chickens in each group were weighed, sacrificed and necropsied. Table III, below shows the results of the tests. Seven 2-(substitutedanilino)benzoxazole compounds were statistically significantly effective at the >0.05 level in increasing weight gains over the infected controls. An eighth compound, Compound A in the table below and within the scope of this invention, produced the third highest average weight improvement of the compounds tested but, because of an abnormally high EMS (error mean square), could not be said to be statistically significant in the test. However, the compound was interpreted to be an effective Marek's disease prophylactic.

Table III

Effect on Weight Gains and Observed Gross Lesions in Chickens Exposed to Marek's Disease when fed Certain 2-(Substituted anilino)Benzoxazoles

| Comp Feed[1] | No. of Chickens in Test | Comp. Level % in Feed (Lbs./ton) | Wt. Improvement per Chicken[2] gm. | Significant at >0.05 Level | Mortality During Test % | Chickens With Lesions At Necropsy % |
|---|---|---|---|---|---|---|
| A | 20 | 0.011 (0.22) | 131.4 | No | 11.0 | 33.0 |
| B | 20 | 0.0055 (0.11) | 122.0 | Yes | 5.0 | 10.0 |
| C | 20 | 0.0055 (0.11) | 102.3 | Yes | 0.0 | 5.0 |
| C | 20 | 0.011 (0.22) | 93.1 | Yes | 10.0 | 10.0 |
| D | 20 | 0.011 (0.22) | 104.3 | Yes | 16.2 | 27.0 |
| E | 20 | 0.0055 (0.11) | 141.5 | Yes | 0.0 | 18.8 |
| E | 20 | 0.011 (0.22) | 96.0 | Yes | 10.0 | 0.0 |
| F | 20 | 0.011 (0.22) | 156.0 | Yes | 0.0 | 20.0 |
| F | 20 | 0.0165 (0.33) | 102.6 | No | 6.3 | 37.5 |
| G | 20 | 0.0055 (0.11) | 116.3 | Yes | 0.0 | 10.0 |
| G | 20 | 0.011 (0.22) | 124.8 | Yes | 5.0 | 15.0 |
| H | 20 | 0.011 (0.22) | 83.8 | Yes | 17.7 | 52.0 |
| H | 20 | 0.011 (0.22) | 99.9 | Yes | 26.3 | 63.4 |
| I | 20 | 0.011 (0.22) | 76.5 | No | 39.5 | 71.1 |
| J | 20 | 0.0055 (0.11) | 72.0 | No | 35.0 | 30.0 |
| Infected Controls | 20 | None | — | — | 29.3 | 47.3 |

[1] A is 2-[4-(trifluoromethyl)anilino 9 benzoxazole
B is 2-[3,5-di(trifluoromethyl)anilino]benzoxazole
C is 2-[2(trifluoromethyl)-5-nitroanilino]benzoxazole
D is 2-[4-bromo-3-(trifluoromethyl)anilino]benzoxazole
E is 2-(2,4-difluoroanilino)benzoxazole
F is 2-(4-phenylanilino)benzoxazole
G is 2-(3,4-dimethylanilino)benzoxazole
H is 2-[4-fluoro-3-(trifluoromethyl)anilino]benzoxazole
I is 2-anilinobenzoxazole, not within the scope of this embodiment of this invention
J is 2-(N-benzylanilino)benzoxazole, not within the scope of this embodiment of this invention.
[2] Difference between the treated and infected control group means.

It will be apparent to those skilled in the art that the useful 2-(substitutedanilino)benzoxazole compounds of this invention can be orally administered to chickens in special feed concentrates, feed supplements, or finished feeds containing one or more of the following ingredients in addition to the nutritive elements incorporated therein: coccidiostats, arsenicals, antibiotics, special vitamins, antibacterials, hormones, growth promoting agents, and the like.

In yet another embodiment of this invention certain 2-(substitutedanilino)benzoxazoles, distinguished by the presence of a $C_1$-$C_4$ alkyl or $C_2$-$C_4$ alkenyl substituent on the nitrogen of the anilino moiety, are effective pre- and post-emergent weed killers. These compounds are characterized by the structure:

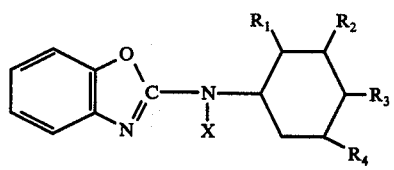

wherein:
X is $C_1$-$C_4$ alkyl or $C_2$-$C_4$ alkenyl;

$R_1$, $R_2$, $R_3$, and $R_4$, when taken singly are hydrogen, bromine, chlorine, fluorine, trifluoromethyl, carboxy, $C_1$-$C_3$ alkyl, $C_1$-$C_3$ alkoxy, $C_1$-$C_3$ alkoxy $C_1$-$C_3$ alkyl, or phenyl, such that only one is phenyl and no more than two of $R_1$, $R_2$, $R_3$, and $R_4$ are other then hydrogen;

$R_5$ and $R_6$, or $R_6$ and $R_7$, or $R_7$ and $R_8$, when taken together constitute the atoms necessary to form a fused aryl ring in either the 2,3- or 3,4-position;

with the proviso that there is a substituent other than hydrogen or alkyl at $R_1$, $R_2$, $R_3$, or $R_4$.

The novel 2-(substitutedanilino)benzoxazoles of this process are excellent pre- and post-emergent herbicides for both weed grasses and selected broadleaf weeds. Moreover, these active herbicidal compounds do not effect agronomic crops such as soybeans. This activity is illustrated by a greenhouse test against ten weed species, including both grasses and broadleaf weeds.

The greenhouse test was carried out as follows: A soil was prepared consisting of one part masonry sand and one part shredded top soil blended together in a cement mixer. Such soil was placed in a galvanized flat 31.5 cm. long 21.5 cm. wide and 8 cm. deep, and was patted down with a bench brush until level. A marker was used to make furrows about 2½ cm. deep. The indicated amount of the following seeds were planted, one species to each furrow.

| Pre-emergence test: | |
|---|---|
| Large crabgrass | 250 |
| Barnyard grass | 100 |
| Lambsquarters | 100 |
| Mustard | 125 |
| Velvetleaf | 50 |
| Wild oat | 25 |
| Foxtail millet | 100 |
| Morning glory | 20 |
| Corn | 4 |
| Soybean | 6 |
| Rice | 35 |
| Sugar Beet | 25 |
| zinnia | 20 |
| Cucumber | 8 |
| Wheat | 40 |
| Alfalfa | 175 |
| Tomato | 45 |

| Post-emergency test: | |
|---|---|
| Large crabgrass | 350 |
| Pigweed | 350 |
| Velvetleaf | 100 |
| Foxtail millet | 200 |
| Zinnia | 20 |
| Corn | 4 |
| Morning glory | 25 |

After planting the seeds are covered with 0.5 to 1.5 cm. of sterilized soil. Two and one-half grams of soluble fertilizer (23-19-17) are applied to each flat during the initial watering.

Each compound to be tested is dissolved in acetone and ethanol (1:1) containing a small amount of surfactant. The solution thus prepared is serially diluted with deionized water containing 1000 ppm of a suitable surfactant to a concentration which will provide in each 12.5 ml. of solution an amount of compound equivalent to an application rate of 1, 2 and 4 pounds of active compound per acre of surface to be treated. Each of the flats in the pre-emergent test are treated with 12.5 ml. of test solution at the concentrations equivalent to 1, 2 and 4 pounds/acre on the day of planting.

The post-emergent plantings are planted 10-13 days before treatment. The flats in which the vegetation is growing which is susceptible to the post-emergent treatment are also treated with 12.5 ml. of solution, each at the concentration equivalent to 1, 2 and 4 pounds/acre. Herbicidal effects are determined 12 to 13 days after treatment. Ratings are based on a 1 to 5 scale as follows:

1 = no injury
2 = slight injury
3 = moderate injury
4 = severe injury
5 = death

Compounds that cause injury ratings of at least one 5 or two 4's are termed active.

The novel compound, 2-[N-(n-butyl)-4-chloro-3-(trifluoromethyl)anilino]benzoxazole, of this invention, useful in the instant process, was tested as described hereinbefore. The data developed in the test is summarized in Table IV, below:

TABLE IV

Herbicidal Activity of 2-[N-(n-butyl)-4-chloro-3-(trifluoromethyl)anilino]benzoxazole

| Species of Plants | Application Rate 1 Lb./Acre | | Application Rate 2 Lbs./Acre | | Application Rate 4 Lbs./Acre | |
|---|---|---|---|---|---|---|
| | Pre-Emergent | Post-Emergent | Pre-Emergent | Post-Emergent | Pre-Emergent | Post-Emergent |
| Alfalfa | 3 | — | 3 | — | 3 | — |
| Corn | 2 | 3 | 2 | 3 | 3 | 3 |
| Cucumber | 2 | — | 2 | — | 3 | — |
| Rice | 2 | — | 2 | — | 2 | — |
| Soybean | 1 | — | 1 | — | 1 | — |
| Sugarbeet | 3 | — | 3 | — | 3 | — |
| Tomato | 2 | — | 2 | — | 2 | — |
| Wheat | 2 | — | 2 | — | 2 | — |
| Barnyard grass | 3 | — | 3 | — | 4 | — |
| Foxtail | 4 | 3 | 4 | 3 | 4 | 4 |
| Lambsquarter | 3 | — | 3 | — | 3 | — |
| Large crabgrass | 4 | 3 | 4 | 3 | 4 | 4 |
| Morning glory | 2 | 2 | 2 | 3 | 3 | 3 |
| Mustard | 3 | — | 3 | — | 3 | — |
| Pigweed | 4 | 3 | 4 | 3 | 4 | 3 |
| Velvetleaf | 2 | 3 | 2 | 3 | 3 | 3 |
| Wild Oat | 3 | — | 3 | — | 3 | — |
| Zinnia | 3 | 3 | 3 | 3 | 3 | 3 |

In the greenhouse test exhibited above 2-[N-(n-butyl)-4-chloro-3-(trifluoromethyl)anilino]benzoxazole was safe on corn at application rates as high as 4 pounds per acre. Severe injury was caused to large crabgrass, foxtail and pigweed in the pre-emergent tests at application rates as low as 1 pound per acre.

The herbicidally active compounds embraced within the scope of this process of the instant invention can either be sprayed onto the soil area in the form of an emulsion, or spread onto the soil area in a solid or granular form. While the surface spraying is an effective method of application of the emulsion, it is preferable that the herbicide should be incorporated into the soil with a power-driven rotary hoe or other similar means to a depth of 1 to 3 inches. The area is then seeded to soybeans or a similar agronomic crop.

The useful compounds of this invention are applied to areas to be seeded with soybeans, or other tolerant agronomic crop at rates varying from about 0.5 to about 8.0 lbs./acre depending on the herbicidal activity of the particular compound and the type of soil.

The compounds can be formulated in either liquid or solid form. A typical emulsifiable liquid concentrate (E.C.) is one containing:
39 percent — 2-[N-(n-butyl)-4-chloro-3-(trifluoromethyl)anilino]benzoxazole
5 percent emulsifier
60 percent higher aromatic naphtha (H.A.N.)
A typical emulsifier is one which contains three parts of the calcium salt of myristylbenzene sulfonic acid to one part of the oleate ester of a polyoxyethylene glycol, having a molecular weight of 350 or thereabouts.

A typical solid formulation is one containing the following ingredients:
5 percent — 2-[N-(n-butyl)-4-chloro-3-(trifluoromethyl)anilino]benzoxazole
8 percent — higher aromatic naphtha (H.A.N.)
87 percent — attapulgite clay (20–40 mesh)
The granules are prepared by dissolving the herbicidal compound in the H.A.N. and spraying the thus prepared solution on the attapulgite clay particles, following standard procedures.

What is claimed is:

1. The method of suppressing the immune response in a warm-blooded mammal comprising administering to said mammal an immune response suppressing amount of a compound of the formula:

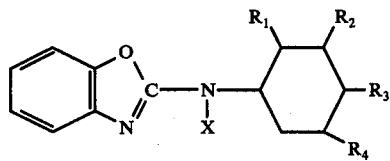

wherein,
X is hydrogen, $C_1$-$C_4$ alkyl, $C_1$-$C_3$ alkoxy, $C_1$-$C_3$ alkoxy $C_1$-$C_3$ alkyl, carboxy, carboxy $C_1$-$C_3$ alkyl, amino $C_1$-$C_3$ alkyl, mono-$C_1$-$C_3$ alkylamino $C_1$-$C_3$ alkyl, di-$C_1$-$C_3$ alkylamino $C_1$-$C_3$ alkyl, anilino $C_1$-$C_3$ alkyl, $C_1$-$C_3$ alkylthio, $C_1$-$C_3$ alkylsulfonyl, phenyl, phenyl $C_1$-$C_3$ alkyl, or carbanilino;
$R_1$, $R_2$, $R_3$, and $R_4$ are hydrogen, bromine, chlorine, fluorine, trifluoromethyl, carboxy, $C_1$-$C_3$ alkyl, $C_1$-$C_3$ alkoxy, carboxy $C_1$-$C_3$ alkyl, $C_1$-$C_3$ alkoxy $C_1$-$C_3$ alkyl, alkylcarbonyl, carb $C_1$-$C_3$ alkoxy, $C_1$-$C_3$ alkylthio, $C_1$-$C_3$ alkylsulfonyl, phenyl, or nitro, with the proviso that no more than one of $R_1$, $R_2$, $R_3$, and $R_4$ is nitro or phenyl, and no more than two of $R_1$, $R_2$, $R_3$ and $R_4$ are other than hydrogen.

2. A method according to claim 1 wherein the compound is 2-[4-bromo-3-(trifluoromethyl)anilino]benzoxazole.

3. A method according to claim 1 wherein the compound is 2-[4-chloro-3-(trifluoromethyl)anilino]benzoxazole.

4. A method according to claim 1 wherein the compound is 2-[4-chloro-3-(trifluoromethyl)-N-n-butylanilino]benzoxazole.

5. A method according to claim 1 wherein the compound is 2-[3-(trifluoromethyl)anilino]benzoxazole.

6. A method according to claim 1 wherein the compound is (3,4-dichloroanilino)benzoxazole.

* * * * *

UNITED STATES PATENT AND TRADEMARK OFFICE
CERTIFICATE OF CORRECTION

PATENT NO. : 4,088,770
DATED : May 9, 1978
INVENTOR(S) : Charles J. Paget, Jr.

It is certified that error appears in the above-identified patent and that said Letters Patent are hereby corrected as shown below:

Column 1, lines 36-37, "2-anilinobenzaxole" should read --2-anilinobenzoxazole--.

Column 2, line 5, "Avain" should read --Avian--.

Column 3, line 55, "2-(4-carboxyanilino)benaoxazole" should read --2-(4-carboxyanilino)benzoxazole--.

Column 5, line 62, after "water.", insert the sentence --The residue was removed by filtration and dried under vacuum.--; and line 62, before "residue" insert --dried--.

Column 6, line 45, after "Analysis:", "$C_4$" should read --$C_{14}$--.

Column 7, line 20, "2-(2,4-difluoroaniline)" should read --2-(2,4-difluoroanilino)--.

Column 8, line 51, insert --EXAMPLE 11--.

Column 13, line 4, "2-[N-carboxymethyl-4-chloro3-(tri-" should read --2-[N-carboxymethyl-4-chloro-3-(tri- --.

UNITED STATES PATENT AND TRADEMARK OFFICE
CERTIFICATE OF CORRECTION

PATENT NO. : 4,088,770

DATED : May 9, 1978

INVENTOR(S) : Charles J. Paget, Jr.

It is certified that error appears in the above-identified patent and that said Letters Patent are hereby corrected as shown below:

Column 14, line 54, under the heading "Mg/Kg X 3", "25" should read --12.5--; and line 56, insert --2-[2-(trifluoromethyl)-5-nitroanilino]benzoxazole--, and under the heading "Mg/Kg X 3" insert --25--.

Column 18, Table II, under heading "4", the third line, "12" should read --5/5--; under heading "5", the third line, "0" should read --12--; under heading "6", the third line, "49" should read --0--; and under heading "7", the third line, insert --49--; and line 42, "or", first occurrence, should read --of--.

Column 21, line 65, "symptons" should read --symptoms--.

Column 22, line 19, under "Percent" heading, "0.6" should read --0.2--.

Column 23, line 48, "are" should read --were--.

Column 24, line 7, "Certain 2-(Substituted anilino)-Benzoxazoles" should read --Certain 2-(Substitutedanilino)-Benzoxazoles--; and line 33, delete "9" and insert --]--.

UNITED STATES PATENT AND TRADEMARK OFFICE
CERTIFICATE OF CORRECTION

PATENT NO. : 4,088,770

DATED : May 9, 1978

INVENTOR(S) : Charles J. Paget, Jr.

It is certified that error appears in the above-identified patent and that said Letters Patent are hereby corrected as shown below:

Column 25, line 5, "then" should read --than--; and line 28, after "Large crabgrass", insert --Pigweed-- --250--.

Column 27, line 18, "39 percent" should read --35 percent--.

Signed and Sealed this

Twenty-second Day of May 1979

[SEAL]

Attest:

RUTH C. MASON
*Attesting Officer*

DONALD W. BANNER
*Commissioner of Patents and Trademarks*